US012626522B2

(12) United States Patent
von Einem et al.

(10) Patent No.: US 12,626,522 B2
(45) Date of Patent: May 12, 2026

(54) INSTRUMENT PARAMETER DETERMINATION BASED ON SAMPLE TUBE IDENTIFICATION

(71) Applicants: STRATEC SE, Birkenfeld (DE); Instrumentation Laboratory Company, Bedford, MA (US)

(72) Inventors: Volker von Einem, Birkenfeld (DE); Timo Ottenstein, Birkenfeld (DE); Jaiganesh Srinivasan, Birkenfeld (DE); Christian Luca, Birkenfeld (DE); Andra Petrovai, Birkenfeld (DE); Dan-Sebastian Bacea, Birkenfeld (DE); Nicoleta-Ligia Novacean, Birkenfeld (DE); Demetrio Sanchez-Martinez, Bedford, MA (US); Mark Wheeler, Bedford, MA (US); Christopher Almy, Jr., Bedford, MA (US)

(73) Assignees: STRATEC SE, Birkenfeld (DE); Instrumentation Laboratory Company, Bedford, MA (US)

( * ) Notice: Subject to any disclaimer, the term of this patent is extended or adjusted under 35 U.S.C. 154(b) by 405 days.

(21) Appl. No.: 18/098,887

(22) Filed: Jan. 19, 2023

(65) Prior Publication Data

US 2023/0230399 A1     Jul. 20, 2023

Related U.S. Application Data

(60) Provisional application No. 63/304,809, filed on Jan. 31, 2022.

(30) Foreign Application Priority Data

Jan. 19, 2022    (LU) ........................................ 102902

(51) Int. Cl.
*G06V 20/69* (2022.01)
*G01N 33/49* (2006.01)
(Continued)

(52) U.S. Cl.
CPC ......... *G06V 20/698* (2022.01); *G01N 33/491* (2013.01); *G06T 5/70* (2024.01);
(Continued)

(58) Field of Classification Search
None
See application file for complete search history.

(56) References Cited

U.S. PATENT DOCUMENTS

2020/0237273 A1* 7/2020 McCormack ......... G01F 23/292
2021/0164965 A1* 6/2021 Ma .......................... G01N 33/49
2022/0178958 A1* 6/2022 Mizutani ................ G01N 35/04

FOREIGN PATENT DOCUMENTS

EP         2148205 B1    1/2013
WO    2018/022280 A1    2/2018
(Continued)

*Primary Examiner* — SJ Park
*Assistant Examiner* — Caroline E. Depalma
(74) *Attorney, Agent, or Firm* — William Gray Mitchell

(57)                    ABSTRACT

A system and method for reducing the responsibility of the user significantly by applying an optical system that can identify container like sample tubes with respect to their characteristics, e.g., shapes and inner dimensions, from their visual properties by capturing images from a rack comprising container and processing said images for reliably identifying a container tyle.

20 Claims, 13 Drawing Sheets

(51) Int. Cl.
  *G06T 5/70*     (2024.01)
  *G06T 7/12*     (2017.01)
  *G06T 7/62*     (2017.01)
  *G06V 10/60*    (2022.01)
  *G06V 10/82*    (2022.01)
(52) U.S. Cl.
  CPC .................. *G06T 7/12* (2017.01); *G06T 7/62*
        (2017.01); *G06V 10/60* (2022.01); *G06V*
        *10/82* (2022.01); *G06V 20/695* (2022.01);
              *G06T 2207/20021* (2013.01); *G06T*
        *2207/20084* (2013.01); *G06T 2207/30024*
                          (2013.01)

(56)                References Cited

FOREIGN PATENT DOCUMENTS

WO      2019/241134  A1    12/2019
WO      2020/219869  A1    10/2020

* cited by examiner

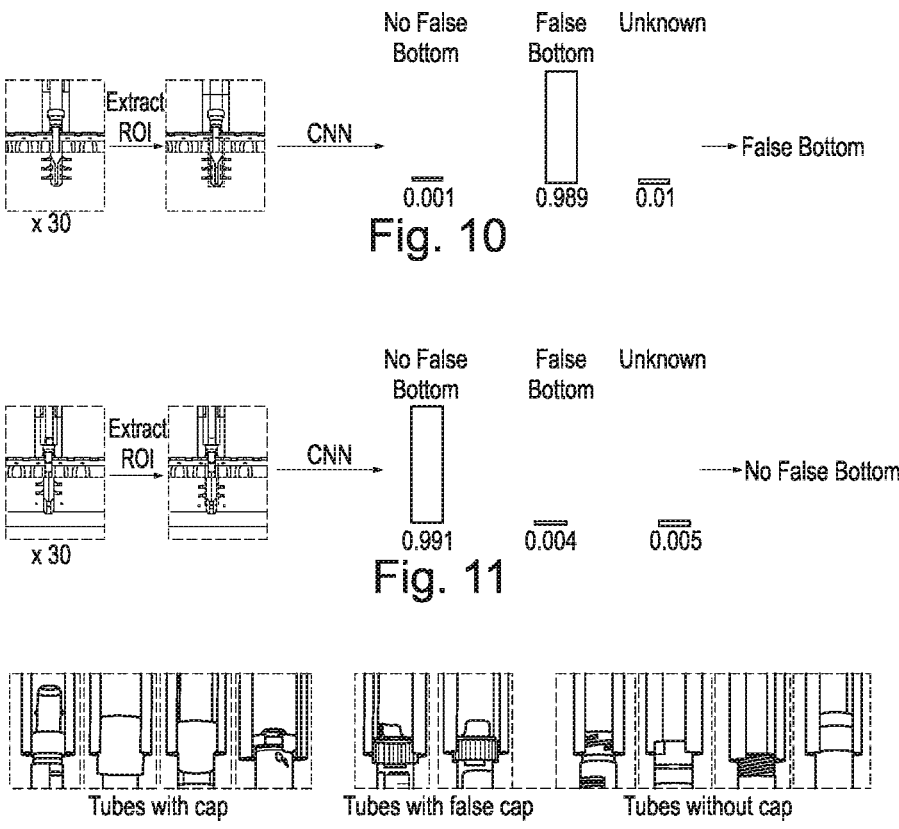
Fig. 10
Fig. 11
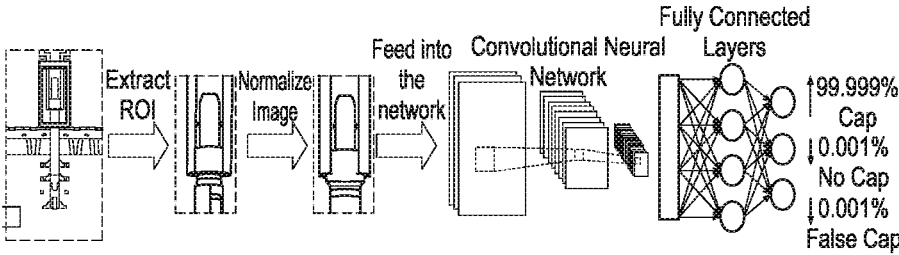
Tubes with cap    Tubes with false cap    Tubes without cap
Fig. 12
Fig. 13

INSTRUMENT PARAMETER DETERMINATION BASED ON SAMPLE TUBE IDENTIFICATION

CROSS-REFERENCE TO RELATED APPLICATIONS

The present application claims priority to Luxembourg Patent Application No. LU 102902 filed on Jan. 19, 2022, and claims the benefit of the filing of U.S. Provisional Application Ser. No. 63/304,809 filed on Jan. 31, 2022. The aforementioned applications are hereby incorporated by reference in their entirety.

BACKGROUND OF THE INVENTION

Field of the Invention

The invention relates to a method for determining the type or class of a container in automated analyser and for determining boundaries of separated layers in a material located in such a container.

Brief Description of the Related Art

Automated analyser systems for use in clinical diagnostics and life sciences are produced by several companies. Such systems perform analytical assays like in vitro diagnostic assays on substantially liquid patient samples comprising body liquids like whole blood samples. The samples are comprised in consumables which will be transported in the automated analyzer systems in racks. The term liquid refers, in the context of the present disclosure, to patient samples (including blood and plasma), buffers, reagents or solutions which may also comprise solids like particles.

The liquids are handled by probes or pipettes. The handling of appropriate liquid volumes is related to the volume of a container like a tube as the volume of a tube depends on its diameter and height.

It is a common task in laboratory instrumentation to aspirate liquids from containers of different kind, like sample tubes, with differing volumes. A liquid's upper surface level depends on a total volume of the liquid in a container, and the container's geometry which depends in turn from height, width, shape, inner diameter and/or bottom height and other differing properties. Additionally, the required liquid filling height has an important impact on the instrument performance within the meaning that a too high liquid level might lead to contaminations, whereas a too low liquid level might lead to insufficient sample aspiration due to a probe that fails to immerge into the liquid.

A consumable sample comprising a sample tube is usually placed into a rack for allowing the movement of the consumable and to keep it in an upright position. The consumable typically projects the upper end of the rack whereas the height of the consumable determines the amount of projection. If different circular containers with an identical height have different diameters, the upper liquid level of a defined volume will differ. This dependency between diameter and height is important with respect to a required liquid level tracking, i.e., the required velocity of a probe following a liquid's upper surface while aspirating.

When placed on a rack, the inner tube bottom is higher than outer tube bottom. Calculating a liquid's upper level using the geometric properties of a wrong tube bottom may result in a too high or too low stop position for the probe.

Thus, the knowledge of the tube bottom geometry is important for avoiding a crash of the probe when moving the probe downwards.

Knowing the upper surface level of a liquid in a tube allows to quickly move the probe close to the surface before liquid level detection (LLD) is activated which requires a slower Z move (up and down) velocity hence resulting in lower throughput.

Knowing the hematocrit of a blood sample prevents an instrument to move a probe too far downwards so that red blood cells (RBC) will be aspirated when only plasma is intended to be suctioned. The aspiration of RBC might lead to wrong results of an assay. Hematocrit (HCT) or Packed cell volume (PCV) is defined by CLSI H07-A3 (Vol 20 N. 18; October 2000) as the measure of the ratio of the volume occupied by the red blood cells (RBC) to the volume of the whole blood, expressed as a fraction. HCT can be also expressed as a percentage.

Existing instruments handle these variations by requiring the user to manually sort tube types of common properties in one specific rack type that is identified by a rack barcode which contains a rack type. An alternative but technically similar approach is to dedicate certain positions within a known rack to specific tube types. In both cases, it is up the user to load a tube into the right rack and or position according to its type which might lead to error conditions due to human mistakes. Health care statistics show that human failure is one of the main reasons for harm on patients related to medical devices.

Published International patent application WO 2020/219869 A1 relates to systems and methods for automatically tailoring treatment of samples in sample containers carried in a rack. The systems and methods may identify sample containers in the rack and/or detect various characteristics associated with the containers and/or the rack. This information may then be used to tailor their treatment, such as by aspirating and dispensing fluid from the sample containers in a way that accounts for the types of the samples/containers carrying them. WO 2020/219869 A1 is silent about the determination of hematocrit.

Published U.S. patent application US 2020/237273 A1 discloses a method based on the use of refraction of a light ray to identify the location of an interface between two materials having different refractive indices. The interface may be an interface between a plasma layer and a red blood cell layer of a centrifuged container, for example. An array of light detector elements is arranged to receive light that has been refracted through different layers in a centrifuged sample. Elements of the light detector array are arranged at known locations relative to an emitter of the light so detection of light by one or more particular detector elements is indicative of the angle of refraction of the light. Vertical position of the sample is tracked and correlated with corresponding angles of refraction to determine the vertical position of the sample when a change in the angle of diffraction is detected. The disclosure of US 2020/237273 A1 is based on the use of refraction of a light array.

Published International patent application WO 2018/022280 A1 discloses a model-based method for determining characteristics of a specimen container cap to identify the container cap. The method includes providing a specimen container including a container cap; capturing backlit images of the container cap taken at different exposures lengths and using a plurality of different nominal wavelengths; selecting optimally-exposed pixels from the images at different exposure lengths at each nominal wavelength to generate optimally-exposed image data for each nominal wavelength; classifying the optimally-exposed pixels as at least being one of a tube, a label or a cap; and identifying a shape of the container cap based upon the optimally-exposed pixels classified as being the cap and the image data for each nominal wavelength. Quality check modules and specimen testing apparatus adapted to carry out the method are described, as are numerous other aspects.

Published International patent application WO 2019/241134 A1 discloses a method for characterizing a serum or plasma portion of a specimen in a specimen container includes capturing a plurality of images of the specimen container from multiple viewpoints, stacking the multiple viewpoint images along a channel dimension into a single stacked input, and processing the stacked input with a single deep convolutional neural network (SDNN). The SDNN includes a segmentation convolutional neural network that receives the stacked input and outputs multiple label maps simultaneously. The SDNN also includes a classification convolutional neural network that processes the multiple label maps and outputs an HILN determination (Hemolysis, Icterus, and/or Lipemia, or Normal) of the serum or plasma portion of the specimen. Quality check modules and testing apparatus configured to carry out the method are also described, as are other aspects.

It is therefore the objective of this disclosure to provide a system and a method for detecting reliably the type or class of a container, respectively its geometry and the related volumetric properties. System and method according to the present may be used for detecting liquid level in a container and/or the hematocrit level in a centrifuged whole blood sample.

SUMMARY OF THE INVENTION

The present disclosure provides a method for determining characteristics of a sample container in an automated testing system, comprising the steps of Identifying the presence of a rack based on information received from a sensor;

Capturing at least one image of the rack;

Determining whether the rack comprises at least one container;

Illuminating each of the at least one container from the side opposite the side of the at least one container where the camera is arranged;

Determining a region of interest (ROI) in the at least one captured image by identifying reference points;

Determining the upper end of the of the rack in the ROI;

Determining of edges an upper end of the at least one container present in the rack within the ROI;

Determining the at least one container's width;

Determining the container's height;

Determining a false bottom of the at least one container by comparing within the ROI the position of the container's lower end with the position of a rack's bottom or a rack's insert bottom;

Determining the presence of a cap;

Determining the type or class of a container by aggregating the results from the group comprising rack type, diameter, height, cap presence, false bottom presence determined in the at least one image's ROI with data of container stored in a database.

In a further aspect of the present disclosure, height and width of each the at least one container are measured at different heights in each image and mean values with standard deviation are calculated for determining a container's dimensions.

The method further comprises the database comprising a set of instrument parameters assigned to a container type or container class.

In another embodiment of the method, the presence of the at least one container is determined by determining intersection points of the rack top and a background illumination by identifying a 2D pixel intensity matrix in different sections in the at least one captured image where the background illumination is present, followed by a first-order differentializing for identifying a slope in the intensity profile.

The method may further comprise a step of convolving the 2D pixel intensity matrix to reduce the noise in the image.

The 2D matrix can be converted to a 1D matrix by taking an average along each row, wherein an intensity plot and variance of the 1D is used for determining the presence of the test-tube.

In another embodiment of the disclosed method, the width for illumination of each of the at least one container from the side opposite the side of each of the at least one container where the camera is arranged is in a range between 15 to 35 mm.

It is also intended that the LEDs for front and back illumination can be arranged in two opposite arranged LED stripes.

The method may also encompass the step of classifying the tube images into one of two classes by a convolutional neural network (CNN).

Another object of the present disclosure relates to a method for determining hematocrit, comprising the steps of:

Capturing at least one image of a rack containing at least one container;

Determining the type or class of the at least one container;

Determining boundaries of separated layers of a material located in the at least one container;

Determining hematocrit based on one or more of layers, liquid levels or liquid volumes percentage of the first layer and the second layer from the bottom in the at least one container.

In a further aspect of a method according to the present disclosure for determining hematocrit, the first layer from the bottom comprises red blood cells and the second layer comprises plasma.

The method may also comprise the step of determining the type or class of the at least one container comprises determining a false bottom of the at least one container by comparing the position of the container's lower end with the position of a rack's bottom end or a rack's insert bottom end.

In a further aspect, the method comprises the step of capturing multiple images of the at least one container during its rotation in front of the camera and forming a segmented picture from the multiple images.

The method may also comprise the step of applying the segmented image to a convolutional neural network (CNN) for determining the upper and the lower boundary of the plasma layer in the segmented picture for generating a bounding box enclosing the plasma layer in all segments of the segmented image.

A further embodiment of the method comprises the step of rearranging the segments of the segmented image prior to determining again the upper and the lower boundary of the plasma layer in the newly arranged segmented picture for generating a bounding box enclosing the plasma layer in all segments of the segmented image.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE FIGURES

The invention will be described based on figures. It will be understood that the embodiments and aspects of the invention described in the figures are only examples and do not limit the protective scope of the claims in any way. The invention is defined by the claims and their equivalents. It will be understood that features of one aspect or embodiment of the invention can be combined with a feature of a different aspect or aspects of other embodiments of the invention, in which:

FIG. 10 shows an example for identifying a false bottom tube.

FIG. 11 shows also an example of a false bottom detection pipeline for a situation where the tube is not a false bottom tube.

FIG. 12 shows an approach collecting a dataset of labeled images for training a classifier.

FIG. 13 shows a training process.

DETAILED DESCRIPTION OF THE INVENTION

The technical problem is solved by the independent claims. The dependent claims cover further specific embodiments of the invention.

A container according to the present disclosure can be a tube, vial, a vessel, a pipette tip, a plate with one or multiple recesses or wells, a microfluidic device or a bottle.

The invention relates to a system for reducing the responsibility of the user significantly by applying an optical system that can identify container like sample tubes with respect to their characteristics, e.g., shapes and inner dimensions, from their visual properties by capturing images from a rack comprising container and processing said images for reliably identifying a container tyle.

Figure 1:
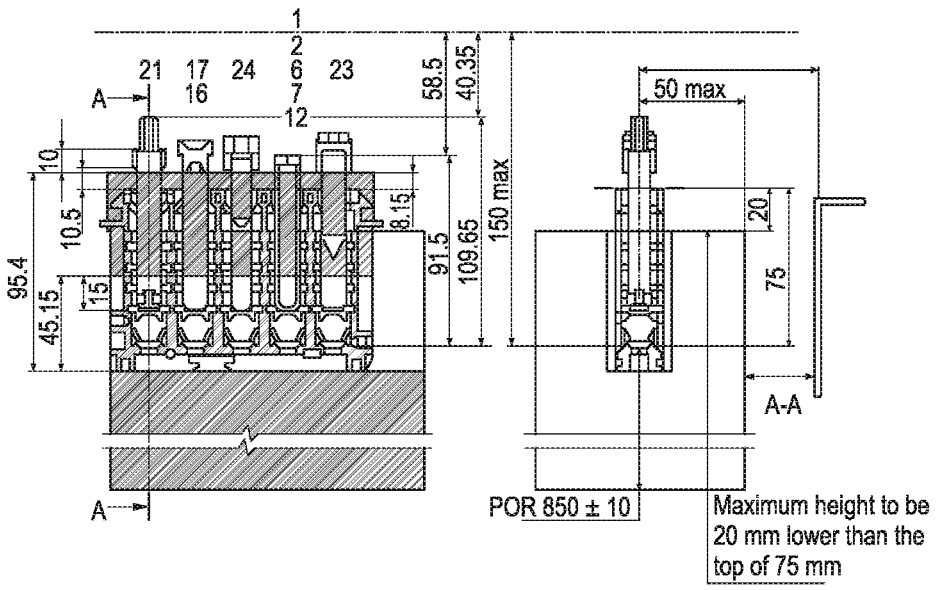
FIG. 1 shows several examples of false bottom tubes.

FIG. 1 shows a rack 10 configured to receive different container 12 types in the same rack 10. Positions 1, 3 and 5 contain so called false bottom tubes. The term false bottom within the meaning of the present disclosure relates to a tube's bottom wall thickness being >3 mm).

The present disclosure relates in a first aspect to a method for identifying a container type or class, like a sample tube for instance. In a further aspect, the present disclosure relates to a method for identifying level of separated layers in a container, which can be used for the Hematocrit assessment.

Figure 2:
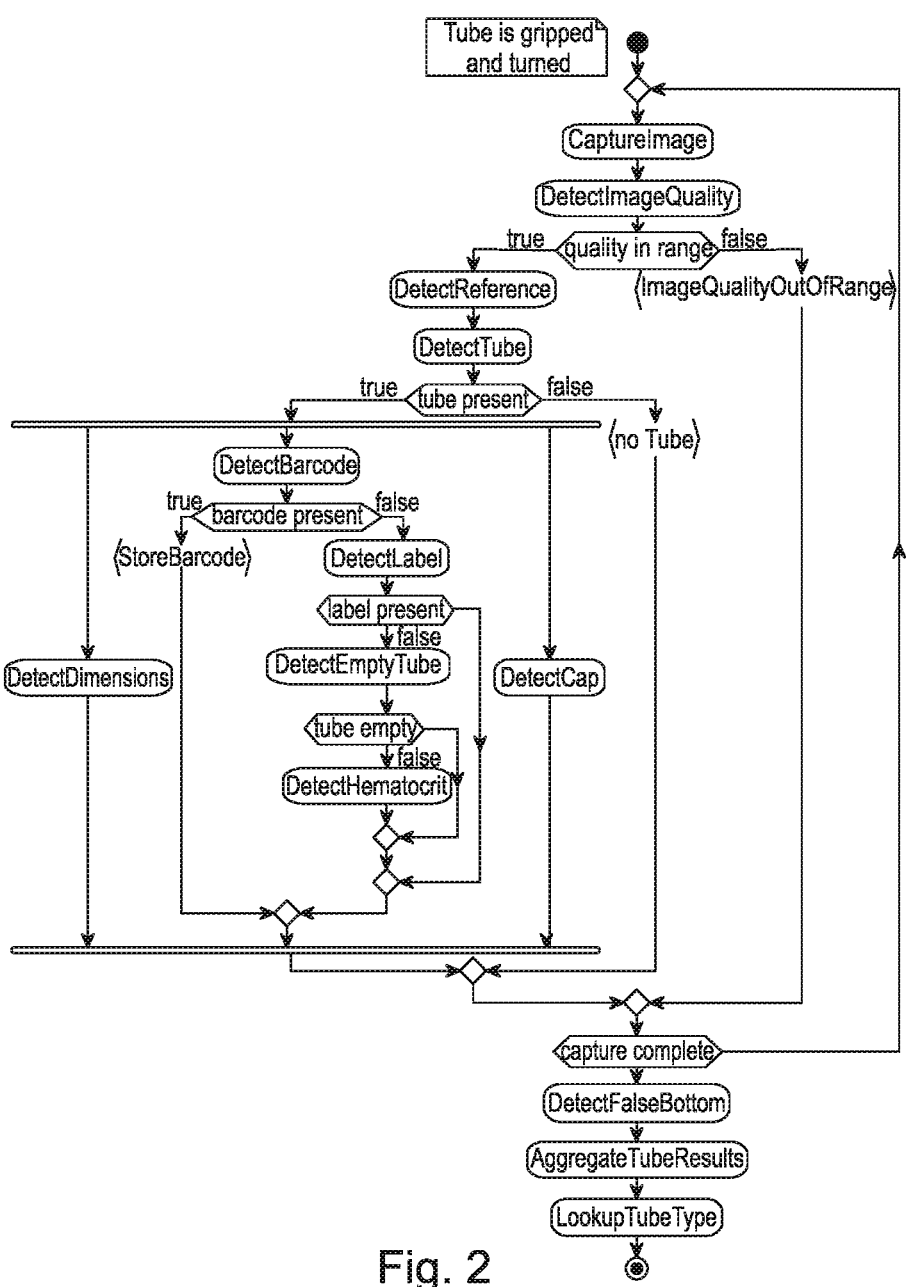
FIG. 2 shows in a flow chart the steps of a method for identifying a container type or class.

The method may comprises the following steps which are also shown in FIG. 2:

1. Providing a tube in front of a camera;
2. Capturing an image;
3. Determining reference points in the image that define relative positions of regions of interest (ROI);
4. Determining the presence of a tube;
5. In parallel:
   5.1. Determining dimensions of the tube, comprising at least height, width, and shape;
   5.2. optionally detecting level of separated liquid layers;
   5.3. detecting the presence of a cap;
6. detecting false bottom properties if images from all angles of the tube are available.

Finally, all results are aggregated, and the container type or class is determined by comparing the obtained data with data stored in a database. During rotation of the tube in front of a camera, multiple images can be captured, and the results are generated for individual images or for all images. Results from individual images are consolidated in a single result. For example, the height of each container is measured in each applicable image and averaged with standard deviation. The width of each container at different heights is also measured in each applicable image and averaged with standard deviation. Cap or no-cap properties are determined. False-Bottom properties are determined. Also, if centrifuged blood is present in the tube, the method can be applied to the establishment of the different levels of the centrifuged blood applying it to the hematocrit assessment.

The overall goal of the methods and systems according to the present disclosure includes finding instrument parameters to safely and accurately pipet liquids from a container like a tube, comprising pipetting only a specific layer in a container or tube. The overall goal can also include providing medical measurements such as hematocrit, from a centrifuged-blood tube automatically, without further manual sample preparation or taking a tube holding the sample off a track or other ways of interfering with the tube's transfer on the track. Data processing and algorithms are applied such that the containers are accurately characterized, and the medical measurements are accurately made.

Figure 3A:
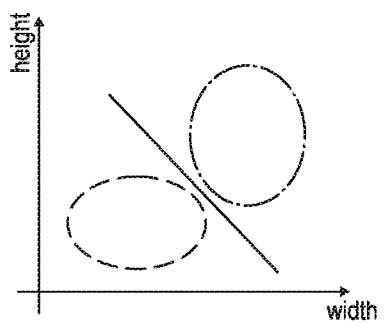
FIG. 3A shows an example where different tube types can be clearly separated from another.
Figure 3B:
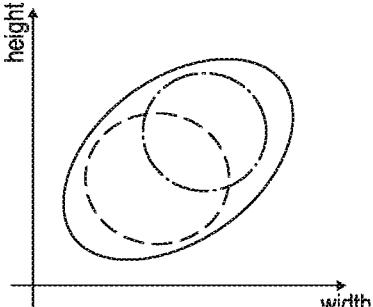
FIG. 3B shows an example where tube types can be merged into a class of tubes with common properties.

A set of instrument parameters can be applied to a single container type of a group or to a class of container types that share similar dimensions. FIG. 3A shows an example, where different tube types can be clearly separated from another and FIG. 3B shows an example where tube types can be merged into a class of tubes with common properties.

Figure 3C:
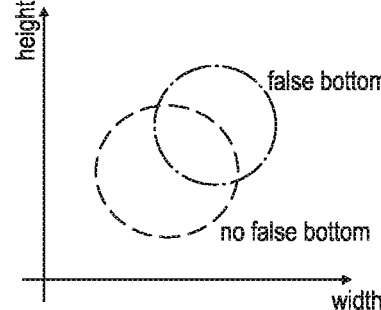
FIG. 3C shows an example for false-bottom tubes.

Some tube types have the same or similar outer dimensions but differ in their inner dimensions. One aspect in this regard are the so-called false-bottom tubes (FIG. 3C). An incorrect determination may result in a probe crash that makes the instrument inoperable until repaired. False bottom container may be difficult to detect due to the bottom being covered by a label. Another problem related to false bottom tube can be caused from an incorrect knowledge of container volumes which will lead to a wrong calculation of a hematocrit boundary. To circumvent this situation a false-bottom indication allows to distinguish between those specific cases.

The methods and systems according to the present disclosure can comprise information about container types or classes, in a database for instance, which are to be queried during determining a container type or container class. The information includes a mapping between one or more characteristics of a container, e.g., instrument parameters such as height or width, along with their tolerance levels, to a type or class of the container. The aggregated results of the in-process container characteristics determination can be used to query the database to identify the type of the container. Only distinctive characteristics (not all) need to be measured to know all characteristics of a container. Mapping in a first step only selectively measured parameters like height, width, etc. allows the system to retrieve all geometric information about the container from the database in a second step. The information is accurate, more accurate than measured ones, such that operations on the container or medical measurements can be accurately performed. This two-step process is advantageous because the system does not need to measure all tube parameters, because they are available from the database which can be extended to provide additional parameters which will not have to be measured in the first step.

The database can be extended with information about new container features and applicable instrument parameters to provide the system with information regarding new container types or container classes used in the field. Additionally, an installation and operational qualification (IQ/OQ) can be performed to ensure a correct differentiation of expected container types or classes.

The optical hardware subsystem for the container identification can perform at least the following tasks:

Illumination of the container (e.g., sample tube) from the front;

(optional) Illumination of the sample tube from the back, which means that the container are illuminated from the side opposite the side of the container where the camera is arranged;

Capturing images of the sample tube with a quality sufficient to perform dimensional measurements and to decode bar- or matrix codes attached to a tube;

In order to meet these requirements, an example optical hardware subsystem can include the following components:

Front illumination system;

(optional)Back Illumination system;

Imaging objective lens; and

Imaging sensor circuit board.

Figure 4A:
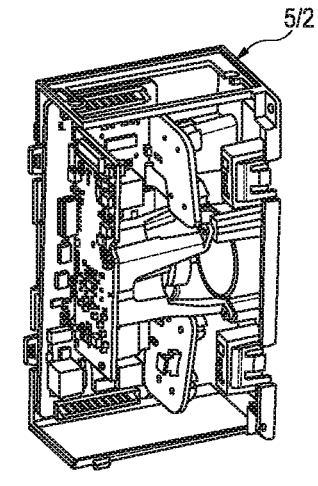
FIG. 4A shows a camera front illumination system according to the present disclosure.
Figure 4B:
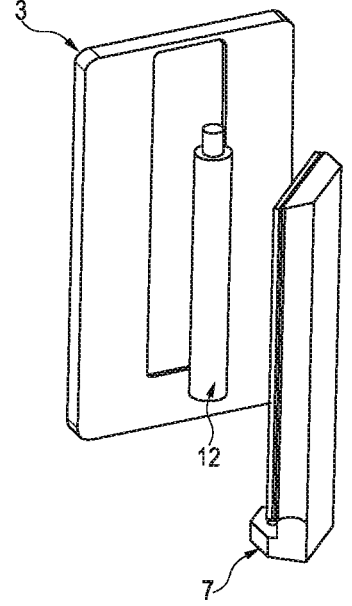
FIG. 4B shows a back illumination system according to the present disclosure.

A possible embodiment of a front illumination system according to the present disclosure is shown in FIG. 4A to FIG. 6. The embodiment in FIGS. 4A and 4B show a camera front illumination system 2 and a back illumination system 3. A container 12 is shown in front of the camera and front illumination system 5, 2. The container 12 is located (e.g., on a track that automatically moves the container) next to the back illumination system 3. A mirror 7 is placed opposite the back illumination system 3 so that the container 12 is located between back illumination system 3 and mirror 7.

In some implementations, a monochrome CMOS sensor can be used. The sensor can have a resolution of 1200×1600 pixels with a pixel size of 4.5 μm can be used in combination with an objective lens with a focal length of 16 mm, although sensors with other suitable, e.g., higher, resolutions can be used. The working distance of the imaging system is roughly 300 mm resulting in a field of view of about 130×100 mm$^2$.

The pixel size in the sample plane which is the imaginary plane at a distance of about 300 mm representing the working distance to the camera can be about 80 μm or less. Such a hardware configuration can allow to differentiate items on the tube like a barcodes with a bar width of about 7.5 mil or larger. Those who are familiar with the art will appreciate that also other combinations of sensor area, pixel sizes and focal lengths are possible, depending on the respective requirements of the application. In particular, the use of a color sensor may be advantageous, in case different colors will have to be detected or distinguished in a container's content or on a container label.

Using a color sensor usually reduces the pixel resolution of the sensor, as a Bayer pattern for realization of the RGB channels is imposed on the pixel array. This reduction of resolution may be detrimental for barcode reading. This can be overcome by accessing each single pixel on the hardware level before the pixel interpolation in the color channels is done. In order to avoid artefacts caused by the Bayer pattern, it is necessary to calibrate the response of each color channel in combination with the used Illumination. As the relative responses of the single-color channels depend on the spectral composition of the illumination it is important to use the same illumination system during calibration than in the later application. The objective lens used in such an embodiment can be a standard catalogue S-Mount objective lens. The method according to the present disclosure is not limited to a hardware configuration of standard objective lenses or S-Mount lenses. Custom designed lenses may have advantages for various applications.

Figure 5:
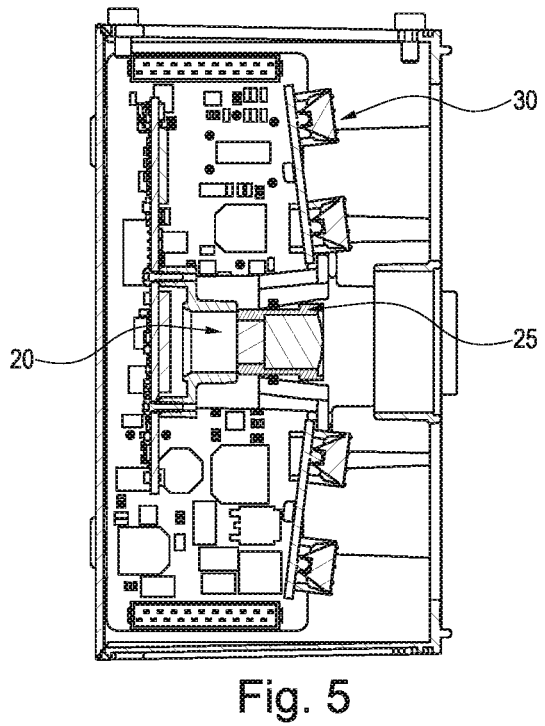
FIGS. 5-6 show embodiments of a front illumination system according to the present disclosure.
Figure 6:
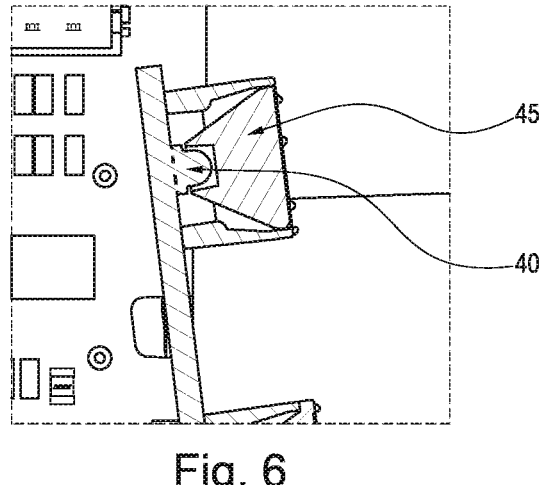

The front Illumination system 2 may comprise four single dye LEDs 40 in combination with standard reflectors 45 (FIG. 6), which are lined up along the long side of the field of view (FOV) and which are symmetrically arranged about the camera subsystem in the embodiment shown in FIG. 6. As indicated in FIG. 5, each pair of reflectors is tilted with respect to the optical axis of the image sensor 20 and image objective lens 25 by around 7 degrees. This results in a rather homogeneous irradiance in the plane of the sample tube. Of course, the angle is dependent on the size of the field of view, the working distance and the collimation of light emerging from the TIR-reflectors (TIR=total internal reflection) and may need adjustment for each application. Those who are familiar with the art will appreciate, that the setup is not limited to the use of standard TIR-reflectors. Custom designs may be advantageous for different application scenarios. The setup is not limited to any color of illumination. Single color or broadband spectral LEDs may be used depending on the application. Broadband LEDs may be advantageously combined with the use of a Color imaging sensor.

FIG. 5 and FIG. 6 do not show polarizers in front of the illumination system in combination with a crossed analyzer in front of the imaging objective lens 25 which are required for reading barcodes. If these polarizers are not included in the setup of a system for performing the method according to the present disclosure, a bright stripe in the middle of the tube can appear due to direct specular back reflection. This bright stripe can reduce the contrast of the barcode in the image significantly. Furthermore, spectral filters in front of the camera, matching the illumination spectrum could be used to suppress disturbances by ambient light.

Figures 7A, 7B, 7C:
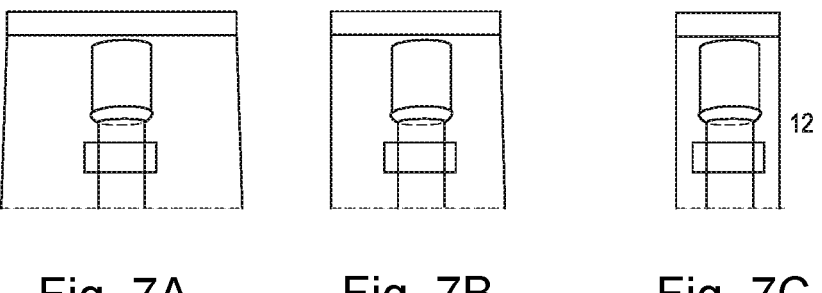
FIGS. 7A, 7B and 7C show embodiments of the back illumination system with different widths of 35 mm, 25 mm and 15 mm.

The back illumination, meaning the illumination of a container from the side opposite the side of a container where a camera is arranged, is used to facilitate the determination of tube characteristics such as the tube diameter. Using the front illumination only in combination with a white reflective surface behind the tube may lead to shadows smearing out the edges of the tub and will thus reduce the precision and accuracy of the measurement. A further important parameter is the width of the back illumination. Example images of the back illumination system with different widths of 35 mm, 25 mm and 15 mm are shown in FIGS. 7A, 7B and 7C.

Aperture within the meaning of the present disclosure refers to the width of the back illumination. The smaller the width of the aperture the stronger becomes the contrast of the tube edges in the images and the more accurate can the tube diameter be measured (left to right in FIGS. 7A-7C). In the present embodiment of the system the aperture can have a width in the range of 25 mm to 35 mm, e.g., 30 mm or less. The selection of an aperture width can be based on multiple factors, e.g., among others, the application, the tube diameter, and the distance between the tube and the back Illumination.

Figures 8A, 8B:
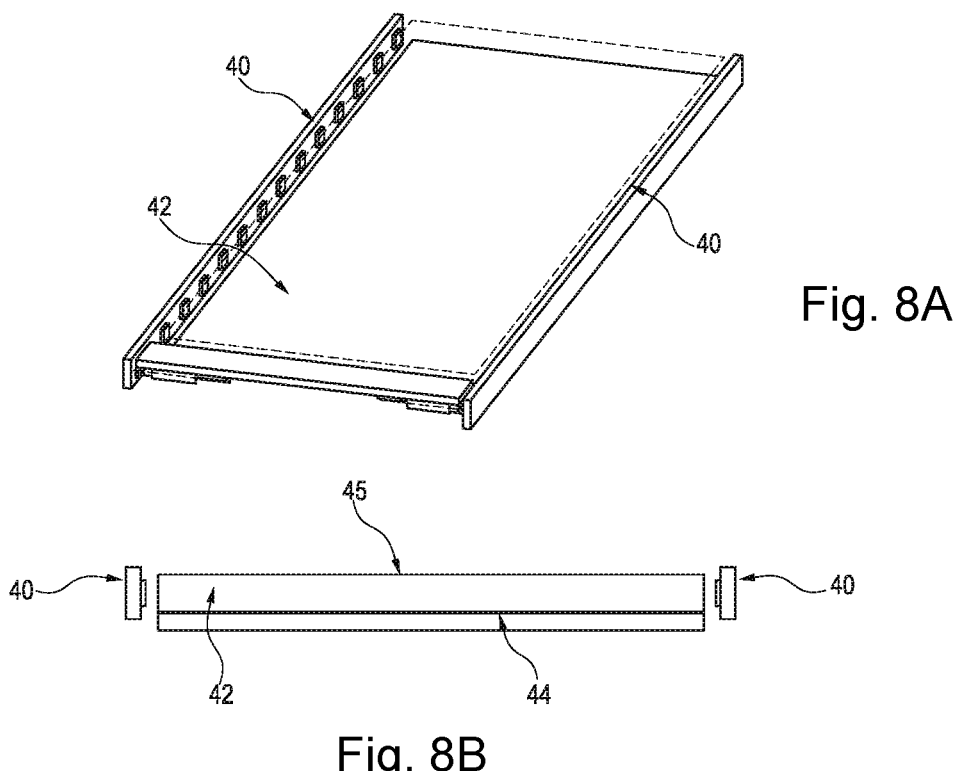
FIG. 8A shows a perspective view of an embodiment with 13 LEDs.
FIG. 8B shows a side view of an embodiment with 13 LEDs.

The back Illumination system comprises two LED stripe circuit boards and a control or supply circuit board, each of them equipped with a set of LEDS. In the example shown in the figure, 13 LEDs (FIGS. 8A and 8B) are used. The subject-matter of the present disclosure is not limited to this exact number of LEDs. Both LED strips can be arranged opposite to each other on the two long sides of a doped Perspex panel. The doping in the Perspex bulk material leads to scattering of light in the material and outcoupling of light from the panel on the front and back side. Without doping, the light may be enter by internal reflection inside the panel and would leave it on the opposite side at the place of the second LED stripe.

PLEXIGLAS 0E010SM by Evonik has been used in an embodiment of the system. The setup is not limited to the use of this material, other materials with similar properties allowing to scatter the LED light for obtaining a homogenous back illumination may also be used. Defined structuring of the plastic panel on the back side, that disturbs internal reflection in a controlled way within the meaning of scattering the light may further improve the light efficiency in terms of emitted lights by the LEDs of the Illumination system. As light can emerge from, both front and back sides of the panel, a white reflective film (KIMOTO Ref White RW188) is used on the back side of the panel. This white film reflects light emerging from the back side back towards the front aperture of the illumination system and enhances the efficiency of the Illumination system. In order to further homogenize the luminance of the system, a diffusing film is put on the front of the panel. Optionally, an additional protection glass can be put on the front of the panel, which is not shown in the figure. The high density of LEDs, the homogeneous doping of the Perspex material in combination with the diffusing film led to a very homogeneous luminance over the output aperture of this back Illumination system. The spectra of the LEDs are not limited to any special color. Depending on the application, single color or spectral broadband LEDs can be used. In the present example white LEDs are used.

As the camera has a fix-focus and due to mechanical and optical tolerances, the system has to be calibrated during production, which means a magnification factor is determined for each system by the use of a known target. This magnification factor is then stored as parameter in the Software and used for all image analysis/calculation steps.

Figure 9A:
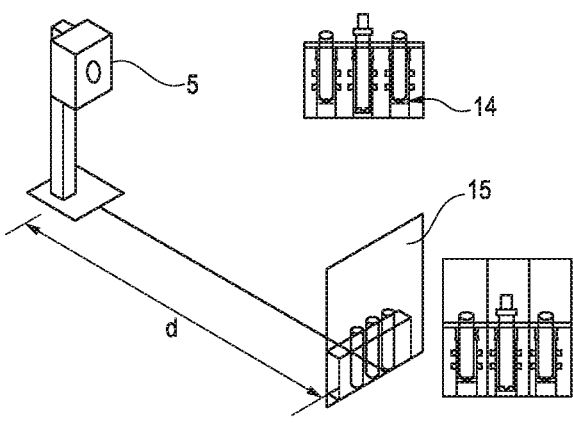
FIG. 9A shows a possible camera setup with a camera, a rack with rack inserts and container which are illuminated from the back with a back illumination system.

The test tube presence detection is part of a sample tube identification method. A test tube presence detection module decides if a step can be skipped because a sample tube is not present. FIG. 9A shows a possible camera setup with a camera 5, a rack 10 with rack inserts 14 and container 12 which are illuminated from the back with a back illumination system 3. The camera can be tilted by 90° clockwise which causes all images of tubes being tilted as well. The back illumination illuminates the top area of a rack.

The method comprises basically the step of scanning a rack with a camera, wherein the rack provides for instance five slots for receiving container or test tubes. Each possible position for a tube is indicated with position markers, e.g. a 2d barcode. A region of interest (ROI) is defined in an area where back illumination is detected and a tube has to be visible if present.

Figure 9B:
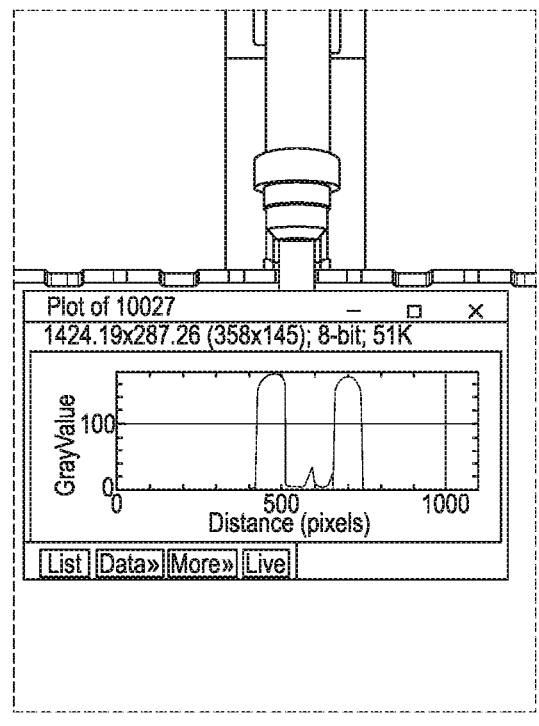
FIG. 9B shows an example for identifying the pixel where the background illumination is present in the image.

The method for the test tube presence detection comprises in more detail the following steps:

1) Identifying pixel with background illumination (FIG. 9B):
   Choosing a column of pixels in one half of the image; and
   Performing a first-order differential for identifying a first slope in an intensity profile of grey values in an image, wherein a first slope indicates a left or right boundary of the background illumination;
2) Identifying a top corner of the rack:
   Choosing a row of pixels on the left or right side of the identified boundary of the background illuminated area; and
   Performing a first-order differential for identifying a second slope in the intensity profile of grey values in an image, wherein the second slope indicates transition from rack to illuminated background thus indicting the top of the rack;
3) Defining the intersection between the line of the identified left or right boundary and the rack top, wherein the intersection represents a corner point which is required for defining a ROI;
4) Defining the ROI starting from corner point, wherein the size of the ROI depends from known mechanical boundaries of the rack;
5) Convolving the 2D pixel intensity with a Gaussian kernel of 5×5 matrix for reducing the noise to signal ratio in the image;
6) Converting the 2D matrix into 1D array by taking an average value along each row; and 7) Determining the presence of a tube from an intensity plot of the 1D array by determining intensity changes in the 1D array.

In some embodiments, the measurement of tube width and height comprises one or more the following steps:

Detection of the region of interest (ROI) as the top area of the image (area above the top rack); this area contains the top part of the tube;

Detection of the edges on the ROI using the Canny algorithm;

Detection of the rack top;

Detection of left profile, right profile and top profile of the tube;

Measurement of tube width at predefined heights above the top of the rack; and

Measurement of the tube height upwards above the rack up to the highest point of a tube's top profile.

The method can be applied to colored and monochrome images.

The present disclosure refers also to the detection of false bottom properties of a container using convolutional neural networks (CNN). Deep learning, when implemented as a supervised learning task, learns a function that maps an input to an output based on input-output examples provided by the user. The function, also called a deep neural network, learns low-level and high-level features from the image, such as edges, corners or shapes and object parts. A classification method classifies the image into a set of predefined classes based on the learned features.

Training a deep learning model is a highly iterative process that includes one or more of the following steps: creation of a high-quality training dataset, design of the ConvNet architecture, training the model, evaluation of the model on the validation dataset. This process can be repeated until the desired accuracy is achieved (e.g., 100%).

Sample tube identification includes detection of false bottom properties. A tube can have a secondary elevated bottom to raise sample level in order to facilitate a more optimal automated analysis. The secondary bottom is also denoted false bottom. The false bottom tubes vary in appearance and false bottom size, defined as the distance between the true bottom and the false bottom. FIG. 1 shows several examples of false bottom tubes with bottom height ranging from 7 mm to 43 mm (position 1, 3, and 5). The presence or absence of a false bottom is detected by processing images of the tubes.

The tube stops at a designated position in front of the camera. The tube is turned 360 degrees and a fixed camera captures multiple, e.g., 10 of the rotating tube. The images are processed, and the tube will be classified as NO FALSE BOTTOM (=0), indicating the absence of the false bottom, or FALSE BOTTOM (=1), indicating the presence of the false bottom. Image classification may be solved using supervised deep learning algorithms. A classification algorithm classifies the image into a set of predefined classes based on the learned features, in our case NO FALSE BOTTOM (=0) and FALSE BOTTOM (=1).

The tube images are classified into one of the 2 classes by a convolutional neural network (CNN), a class of deep neural network algorithms. The CNN receives a batch of, e.g., ten images of the tube. The images are grayscale and have a size of 10 (images)×H×W, where for example H=1536 pixels, W=2048 pixels. The images are cropped relative to the position code with the region of interest (ROI) of size H'×W', which contains the bottom half of the tube. The ten ROIs are concatenated along the channel dimension. The input to the CNN network is the batch of B (batch)× 10×H'×W' images, where B=1 during inference and B>=1 during training. CNNs perform image feature extraction by applying convolutional operations with filters, whose parameters are learned in the training process. A ConvNet stacks a variable number of convolutional layers and activation functions such as ReLU and learns basic features such as corners, edges at initial layers, while complex high-level features are learned at deeper layers. A classification algorithm such as SoftMax takes as input the extracted features and outputs a normalized probability distribution of the predefined classes. The class with the highest probability is chosen as the class of the tube.

FIG. 10 shows an example of a false bottom detection pipeline when a container like a tube is a so-called false bottom tube. A batch of ten images has been processed by the CNN and the CNN outputs a normalized probability distribution of the classes. The tube is classified as false bottom since the probability for the false bottom class is the largest.

FIG. 11 shows also an example of a false bottom detection pipeline for a situation where the tube is not a false bottom tube. A batch of ten images has been processed by the CNN and outputs a normalized probability distribution of the classes. The tube is classified as no false bottom since probability of then no false bottom class is the largest.

Each image can be annotated with one of the labels: NO FALSE BOTTOM (=0), FALSE BOTTOM (=1). Training may be done on as many images as necessary to achieve a good accuracy. Using the available dataset, a training and a validation dataset are to be created. Around 80% of the data goes to the training set and 20% of the data to the validation set. In the training phase, the network sees examples only from the training set and learns the weights based on the training image-label samples. To evaluate the performance of the network, the accuracy on the validation set has been computed, which contains unseen examples. If the accuracy on the validation set is not satisfactory, which should be close to 100%, more samples can be added to the training set and the network can be re-trained. Then, the network will be evaluated again on the validation set. The training process can be stopped when the desired accuracy in determining the correct label of an image is reached.

In the training process, one or more batches of multiple, e.g., 10, images with their associated labels are randomly sampled from the training set. A Region of Interest (ROI) with the bottom of the tube is extracted from each image. The image ROIs are passed through the network and the loss function is calculated, which measures how close the predictions are compared to the training labels.

The training process can be done in any suitable deep learning frameworks: TensorFlow, PyTorch, or MXNet.

A CNN network architecture according to the present disclosure is made of residual blocks, pooling operations and fully connected layers. Residual blocks learn residual functions with respect to the input layer and facilitate convergence especially in the case of deeper networks. First, the network is comprised of two Convolutions, Batch Normalization, ReLU activation, that computes features at half input resolution using 32 filters. The convolution filters have a small receptive field of 3×3 and the stride is set to 2 for the first convolution to perform down sampling and 1 to the second convolution. The spatial padding has been set to 1 for 3×3 convolutions to preserve the spatial resolution after convolution. Spatial pooling followed using maximal pooling layers with a filter size of 3×3 and stride 2. The residual blocks are comprised of two [3×3] convolutions, batch normalization layer and ReLU activation. A shortcut connection between the input and output of the block has been introduced, which are identity shortcuts when the input and output have the same size and a projection shortcut with a 1×1 convolution to match the dimension when sizes differ. At each layer following the spatial pooling two residual blocks have been added. Layers [4-6] perform down sampling with the first convolution in the first residual block having a stride of 2. In order to ensure the low complexity of the model, the number of learned filters is small and increases from 32 to 128 in the last layer of the network. Finally, an average pooling and a fully connected layer are applied that yield the logits for the 2 classes. Softmax is the last layer of the network, which assigns a probability to each class and represents the likelihood of the image to belong to that class. The reported class for an image is the class with the highest probability.

TABLE 1

Summary of the architecture of the Convolutional Neural Network.
Input and output size format: Batch Size × Height ×
Width. Filters: [filter height × filter width, number of filters, stride].

| Layer | Input size | Output size | Filters |
|---|---|---|---|
| 1 | 10 × 75 × 255 | 10 × 38 × 128 | [3 × 3, 32, 2], Batch normalization, ReLU [3 × 3, 32, 1], Batch normalization, ReLU |
| 2 | 10 × 38 × 128 | 10 × 19 × 64 | [3 × 3, —, 2] MaxPooling |
| 3 | 10 × 19 × 64 | 10 × 19 × 64 | Residual block: [3 × 3, 32, 1], BN, ReLU, [3 × 3, 32, 1], BN, ReLU Residual block: [3 × 3, 32, 1], BN, ReLU, [3 × 3, 32, 1], BN, ReLU |
| 4 | 10 × 19 × 64 | 10 × 10 × 32 | Residual block: [3 × 3, 64, 2], BN, ReLU, [3 × 3, 64, 1], BN, ReLU Residual block: [3 × 3, 64, 1], BN, ReLU, [3 × 3, 64, 1], BN, ReLU |
| 5 | 10 × 10 × 32 | 10 × 5 × 16 | Residual block: [3 × 3, 128, 2], BN, ReLU, [3 × 3, 128, 1], BN, ReLU Residual block: [3 × 3, 128, 1], BN, ReLU, [3 × 3, 128, 1], BN, ReLU |
| 6 | 10 × 5 × 16 | 10 × 3 × 8 | Residual block: [3 × 3, 128, 2], BN, ReLU, [3 × 3, 128, 1], BN, ReLU Residual block: [3 × 3, 128, 1], BN, ReLU, [3 × 3, 128, 1], BN, ReLU |
| 7 | average pool, fully connected layer, softmax | | |

The network is trained end-to-end with one optimization step. The implementation has been tested on the false bottom dataset. In all experiments, the network with Kaiming Uniform method has been initialized. The network is trained with a mini-batch of samples and Adam optimizer. The weighted cross entropy loss is minimized during training. In order to solve class imbalance, the loss is weighted by the inverse class frequency.

Detecting the presence of caps for sample tubes is important for the control system. This information is used for aiding the pipetting process. Tubes inserted into the system may have cap, no cap or a special type of cap called "false cap". False caps are a particular type of caps which are hollow on the inside but given the perspective from which the tube is observed, the hollowness is not visible. Tubes with such caps are considered to be without cap and the system should identify them appropriately. For each container, like a sample tube, one or 10 images (360 degrees turning) may be acquired. The acquired image(s) are processed and will be classified as: NO CAP (=0), CAP (=1), FALSE CAP (=2). For solving this task a data driven approach may be used, such as machine learning. This approach requires collecting a dataset of labeled images, which is used for training a classifier which can operate with high accuracy on images it has never seen before (FIG. 12)

For detecting the presence of caps, a region of interest (ROI) containing the upper part of the tube shall be extracted from the full-sized image. The ROI is then processed through a normalizing procedure, which involves rescaling the pixel values to be in the interval [0-1] followed by centering the values to have zero mean and unit variance. The obtained image can then be classified using support vector machine (SVM), tree-based classifiers (e.g. decision trees), adaptive boosting classifiers (e.g. Adaboost) or artificial neural networks (e.g. Convolutional Neural Networks (CNN)). The approach taken in this implementation is based on CNNs, the obtained image is inserted into a CNN which classifies the input image. The output of the CNN is a probability distribution over all the possible pre-defined classes, which are cap, no cap, false cap. In the training process, the network is adjusting the connection strengths between its layers such as the probability assigned to the correct class will be maximized, while the probabilities assigned to the other classes will be minimized. (FIG. 13)

Figure 14:
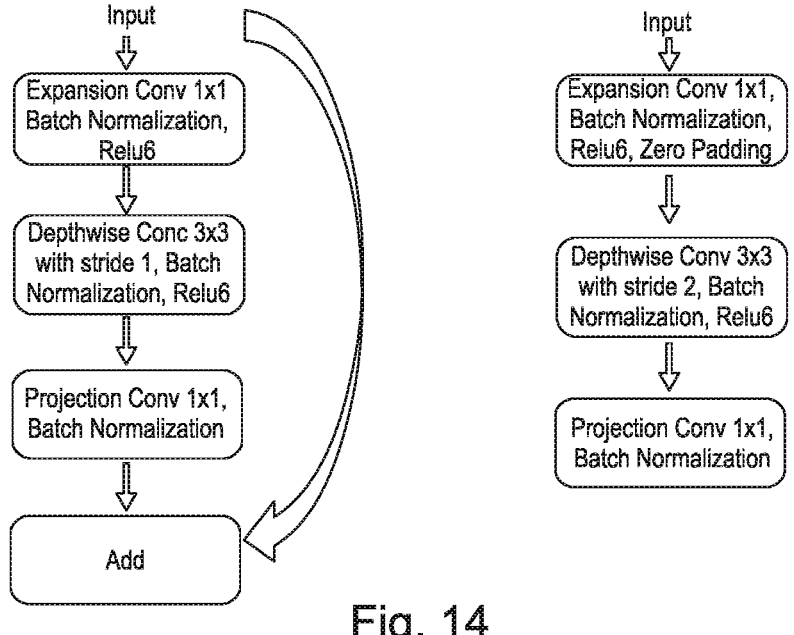
FIG. 14 shows training of a CNN.

For training the CNN, a dataset containing multiple reference images for each supported container type is constructed. According to each container specific characteristics, reference images are acquired for the container with cap, without cap and with false cap (if false cap is a characteristic of the tube type). All the images are labeled with one of the pre-defined classes and each image is added inside the appropriate class directory. The dataset is then split again in two parts, the training set (e.g., 80%) and the test set (e.g., 20%). The images in the training set are used for fitting the model in the training process (adjusting the weights of the neural network). The images in the test set help providing an unbiased evaluation of how good of a fit the model achieved after training on the training set (FIG. 14).

The dimensions of the initial acquired images are H×W× 1, with H=1536 pixels and W=2048 pixels. For each image the ROI is extracted, which has the dimensions 350 pixels× 675 pixels×1 which will be the input for the neural network. The output of the classification algorithm is a probability distribution, which can be achieved using a function that output normalized probability distributions, such as Softmax. To achieve a CNN that is robust to variations of the images (e.g., brightness, contrast, noise), data augmentation is used in the training process. During training, before feeding an image as input to the neural network, random flipping, random brightness and/or contrast variations are applied. The training process is continued until a sufficiently high accuracy is obtained (nearly 100%). The network is trained end-to-end with a mini batch of 64 samples from the Cap_NoCap_FalseCap dataset.

Figure 15:
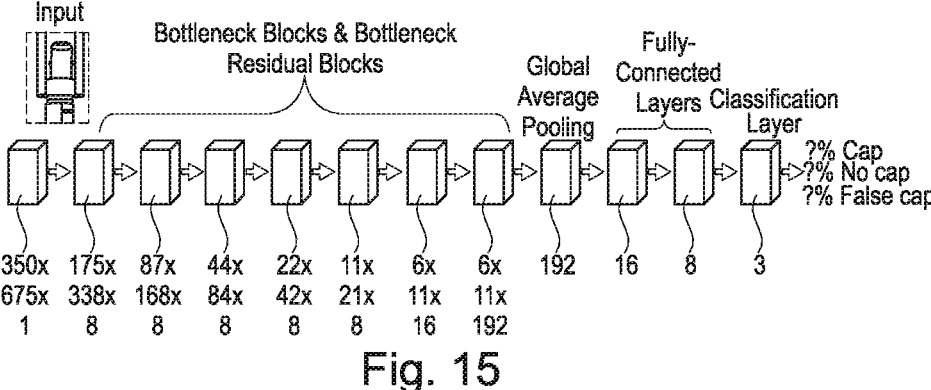
FIG. 15 shows the architecture made of bottleneck and bottleneck residual blocks.

The architecture can be made of multiple, e.g., 10 or more, 15 or more, or 17, bottleneck and bottleneck residual blocks followed by one or more global average pooling layers and one or more, e.g., 2, fully connected layers, the last fully connected layer being the classification layer or keeping the amount of computation and memory footprint low, the first layers in the neural network architecture are 2 blocks of "Convolution-Batch Normalization-Relu6", the convolutions being performed with a stride of 2, thus reducing the dimensionality of the input by a factor of 4. Another optimization for efficiency that was used consisted of setting the expansion factor in the first 6 bottleneck residual blocks to equal 4, while for the last two bottleneck layers it equals 6. The total number of feature maps in the last bottleneck residual block is kept to 192. The total number of parameters of the neural network model is 20.243, out of which 18.435 are trainable parameters (FIG. 15).

The detailed CNN architecture used for detecting the presence of Cap_NoCap_FalseCap is presented in Table 2. It can be implemented using any suitable computing framework or toolbox, such as Tensorflow, Pytorch, or Keras.

the generated models is above a target accuracy (e.g. 98%) and if the standard deviation is smaller than a target sigma value (e.g. 1).

The obtained model is then evaluated on the test set to see if it operates at a sufficiently high level of confidence (e.g., greater than 98%). For each prediction, it is first evaluated if the confidence value (out of the three output probabilities of the network, the one with the highest value) is greater than a defined threshold (e.g., 0.5). If the confidence value is below this threshold, then the prediction of the network is considered to be uncertain. The number of predictions with small confidence on the test set is then counted. The lower the number of predictions with small confidence, the better

TABLE 2

| CNN architecture used for detecting the presence of Cap_NoCap_FalseCa | | | | |
|---|---|---|---|---|
| Type | Input size | Output size | Output Channels | Expansion Factor |
| Input block (Zero Padding, Conv2D with 3 × 3 and stride 2, Batch Normalization, Relu6) | 350 × 675 × 1 | 175 × 338 × 8 | 8 | — |
| Downsampling block (Conv2D with 3 × 3 and stride 2, Batch Normalization, Relu6) | 175 × 338 × 8 | 87 × 168 × 8 | 8 | — |
| Bottleneck residual block 1 | 87 × 168 × 8 | 87 × 168 × 8 | 8 | 1 |
| Bottleneck block 1 | 87 × 168 × 8 | 44 × 84 × 8 | 8 | 4 |
| Bottleneck residual block 2 | 44 × 84 × 8 | 44 × 84 × 8 | 8 | 4 |
| Bottleneck block 2 | 44 × 84 × 8 | 22 × 42 × 8 | 8 | 4 |
| Bottleneck residual block 3 | 22 × 42 × 8 | 22 × 42 × 8 | 8 | 4 |
| Bottleneck block 3 | 22 × 42 × 8 | 11 × 21 × 8 | 8 | 4 |
| Bottleneck residual block 4 | 11 × 21 × 8 | 6 × 11 × 16 | 16 | 6 |
| Bottleneck block 4 | 6 × 11 × 16 | 6 × 11 × 16 | 16 | 6 |
| Conv Output block (Conv2D with 1 × 1 and stride 1, Batch Normalization, Relu6) | 6 × 11 × 16 | 6 × 11 × 192 | 192 | — |
| Global Average Pooling | 6 × 11 × 192 | 192 | — | — |
| Fully Connected Layer 1 (with Dropout(0.4) and with Relu activation) | 192 | 16 | — | — |
| Fully Connected Layer 2 (with Dropout(0.4) and with Relu activation) | 16 | 8 | — | — |
| Fully Connected Layer 3 (with softmax) activation | 8 | 3 | — | — |

For validating that the proposed architecture and the training procedure can generate models that work at a sufficiently high accuracy when new container types or classes are introduced in the system, k-fold cross validation is used. It provides a robust estimate of the performance of the model on unseen data. In k-fold cross validation the dataset is partitioned into k equal-sized subsets. Out of the k subsets, one subset is retained as the validation data for testing the model, and the remaining k-1 subsets are used as training data. This process is repeated k times, with each of the k subsets being used exactly once as the validation data, thus generating k models. The performance measures (e.g. accuracy) obtained in each iteration are then averaged across all created models and standard deviation is computed, providing a less biased estimate of the performance achieved using a specific architecture and training procedure.

The container from the container database (which contains all the container containers supported by the system) are split into k subsets, where k is the number of supported container, each container type being used as the validation data once. An even more robust estimate is obtained when more container types are held out in one iteration for validation (e.g. out of the k container types, two or more container types can be held out for validation in each iteration). The model is accepted if the average accuracy of fit the model has on the task. The predicted class is selected as the output probability with the highest value. If the predicted class is different from the expected correct class, then the number of errors on the test set is incremented. For better assessing the confidence and the quality of the predictions a new metric called confidence margin will be evaluated. For each output of the network, the difference between the highest probability value and the second highest probability value is computed. This metric helps at assessing if the features found for an input image are representative enough to discriminate it from the features specific to other classes. A low confidence margin means that the network is uncertain in its prediction and cannot discriminate between classes, so further images of that kind shall be acquired and the model trained on them. The minimum, maximum and average confidence margin is assessed on the test set for the correct predictions, the incorrect predictions and for the predictions with small confidence. For the correct predictions the minimum confidence margin should be as high as possible, the average confidence margin should be above a pre-defined threshold (e.g. 0.5) and the maximum confidence margin should be close to 1.0. For the incorrect predictions, the minimum confidence margin should as small as possible, the average confidence margin should be as small as possible, the maximum confidence margin should be as low as possible, conditions if satisfied then such incorrect predictions are discarded. Predictions with small confidence value are discarded as well.

Liquid level detection, based on which hematocrit can be determined for samples in a container, is also an object of the present invention. The input is a container like a sample tube comprising a centrifuged sample. The container can be rotated in front of a camera to generate a number of images (images/rotation). The images can be used to determine the tube characteristics as described above, and can also be used for detecting the liquid levels within the tube, e.g., the total liquid level, the interface between the plasma -and the red blood cells level and the bottom of the red blood cells level First, images showing container which do not have a barcode or a label are further processed to detect if the test-container is empty or not.

For empty container detection, the images are processed to check whether the test container is empty or not; if the test container is empty, the sample container feature extraction steps can be skipped. A sample container with a blood sample has a higher variance in intensity than the sample container that is empty. Statistical parameters such as variance and CV (coefficient of variation, is defined as the ratio of the standard deviation to the mean) are used to define the flatness of the intensity profile within the sample-tube to identify if the sample-tube is empty or not.

Real centrifuged blood samples with different % Hct (hematocrit) values and blood challenges were used to establish a clear line of separation between red blood cells and plasma. White illumination was used as a front illumination to make the red blood cells to be dark and the plasma to be bright in the image.

In an initial step, an ROI-smoothed image is generated with a Gaussian filter of 5 pixels by 5 pixels which is convolved to eliminate noise in the taken image. Based on the kernel size and the filter type applied the results can deviate to [by?] one or two pixels.

Figure 16A:
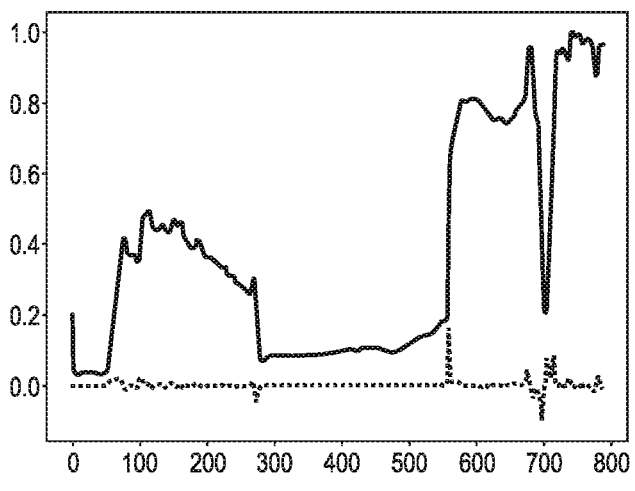
FIGS. 16A and 16B show a curve with a negative slope of the intensity values decreasing from a higher value to a lower value.
Figure 16B:
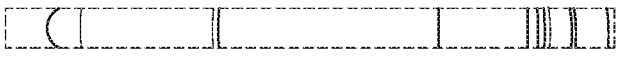

Next, one or more the following steps can be performed:
dimension reduction: The ROI-image which is a 2d (two-dimensional) array of intensity values is reduced to a 1d (one-dimensional) array, e.g., by summing all the column or row values together so that they become a single row and multiple, e.g., over 700, over 750, or 787, columns or a single column and multiple rows.
Normalization: the 1D array is normalized, e.g., with the maximum value, from the array;
Differentiation: A first-order differential of the normalized array is computed, where the maxima and minima define the different liquid levels in the container, e.g., the bottom liquid level or blood level and the too liquid level or plasma level, respectively. In particular,
i. Bottom level is a liquid level at which a transition from the bottom liquid component, e.g., blood cells, to the top liquid component, e.g., plasma, takes place. Such a transition is represented by a positive slope of the intensity with a pixel value between 0-255, because the image intensity value increases from a lower value to a higher value.
ii. Top level is a liquid level at which a transition from top liquid component, e.g., plasma, to the empty space, e.g., air, in the test-tube takes a place. Such a transition is represented by a negative slope of the intensity with greyscale values between 0-255 because of the concave nature of the top of the liquid component (due to building a meniscus which is concave) as the image intensity value decreases from a higher value to a lower value (FIGS. 16A and 16B).

iii. Accordingly, the maxima and minima of the differentiated array provide information about the geometric locations the bottom liquid level and top liquid level within the sample container.

There are two potential types of interferences:
A) Interferences that can impact the correct assessment of the levels essential to calculate the Hematocrit:
A1) Bottom level of the RBC due to deficient establishment of the real RBC bottom level (e.g.: not distinguishing the color of the RBC from the bottom of the tube/rack shelf);
A2) Interface level between the RBC and White cells/plasma due to not distinguishing the difference in color because interferents in the plasma produce color similar to RBC (e.g.: high concentration of lipids, or/and hemoglobin, or/and bilirubin); and
A3) Top level of plasma, this level can be difficult to identify if its color is not clearly differentiated form the color of the tube.

For these three cases, real centrifuged blood samples, with the above-mentioned interferents, and different Hematocrit concentrations are used to challenge the algorithm to find out and improve its reliability to identify the described levels.
B) Interferences that can prevent the detection of the above-explained levels due to physical impediments, including but not limited to labels covering the whole surface of the tube, printed graphic/lettering on the tube, and others. If the tube does not have a minimum sliver of room to reliably detect the above-mentioned levels; then, the Hematocrit will not be possible to assess and the result will be given as undetectable.

TABLE 3

Summary of possible interference from illumination.

| Illumination | Pros | Cons |
|---|---|---|
| Blue | — | 1. Not suitable for animal blood |
| Yellow | 1. Distinguishes red blood cells (RBC) and plasma<br>2. Easy to identify the meniscus of the plasma as it is thin | 1. No clear separation between RBC and white blood cells (WBC)<br>2. Requires long exposure time 500 microseconds |
| Amber | 1. Distinguishes RBC and plasma<br>2. Clear separation between RBC and WBC<br>3. Std-dev of the signal seems to be lesser than the yellow illumination | 1. Often penetrates through the label on the test tube and increases the complications<br>2. Hard to find meniscus of the plasma, because a thick layer of the meniscus is seen |
| IR | 1. Lesser exposure time<br>2. Less current consumption | 1. No clear separation between RBC and WBC |

In some implementations, a first-order derivative of the reduced, normalized array as described above may not be appropriate when there is no clear separation between the liquid components, e.g., RBC, vs WBC/, and the plasma. For example, each region of the image may seem to fall in a certain category of intensity level, because they have the same intensity level. If the WBC or the buffy region is too thick or if a clear boundary between buffy region to the plasma is not clearly visible, then in the image we see a gradual transition in the intensity. Such a situation makes it hard to define a clear level detection of plasma. In some implementations, a histogram can be constructed to show the distribution of intensity.

Figure 17:
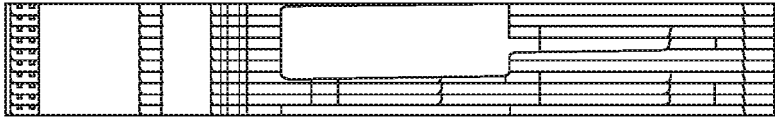
FIGS. 17 and 18 show an example for determining the plasma portion in a test specimen.

For determining hematocrit, the container stops at a designated position in front of the camera. The container is turned 360 degrees and a fixed camera captures multiple, e.g., ten images of the rotating tube. In an embodiment, from each image, a region of interest (ROI) can be generated relative to the position code. Generally, for detecting the hematocrit levels, a custom image is generated by vertically stacking the ten images (FIG. 17). To determine the hematocrit, the tube's geometric information, e.g., shape, dimensions, etc., and liquid levels can be determined whether by a user input or by determining the container type as described above, so that for the geometric information, in one embodiment, the above-described systems and methods for determining container parameters can be used. For the total liquid level and the plasma/red blood cell separation liquid level, the above-described liquid level determination methods can be used. From the tube geometric information and the liquid levels, the volume of the liquid portion that contains the red blood cells (Volume_red) and the total volume (Volume_total) of the liquid in the tube can be calculated. The ratio of Volume_red and Volume_total is the hematocrit level of the liquid in the tube.

Figure 18:
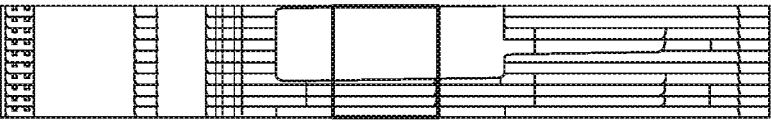

FIG. 17 and FIG. 18 show an example for determining the plasma portion in a test specimen. As already mentioned, multiple pictures of the container are captured, wherein the container is rotated so that the multiple pictures are taken from different perspectives. Each horizontal line in FIG. 17 and FIG. 18 represents a single picture as shown in FIGS. 16A and 16B. The container has been rotated ten times in front of the camera so that ten pictures have been capture in the example shown in FIG. 17 and FIG. 18 forming the single picture of FIG. 17 and FIG. 18 comprising a kind of ten horizontal stacked segments. It has to be noted that each image shows the container rotated by 90°.

The top and bottom edges of the plasma comprising layer is marked, which is indicated in FIG. 18 with a square in the middle of the picture. Plasma portion detection can be viewed as a specific case of the object detection problem which has been described above—bounding box regression and classification which describes the spatial location of an object. The bounding box is rectangular, which is determined by the xx and yy coordinates of the upper-left corner of the rectangle and the coordinates of the lower-right corner of the rectangle. The left and right boundary of the bounding box indicate and correspond to the upper and lower ends of the plasma layer due to the 90° rotated image. With respect to the present disclosure, only the width of the box is detected while the height is fixed and is equal to the height of the image.

For determining the type or class of the container during hematocrit determination, the above described methods for determining characteristics of a sample container in an automated testing system are also applicable.

More specifically, a convolutional neural network (CNN) is created that takes as input an image like that in FIG. 17 and detects if plasma is present in the image and if so, it generates a localized bounding box around the plasma portion. The cost function used for training the CNN is modified to ignore error computation for the Y axis coordinate and for the height of the bounding box. Thus, in the present disclosure, only the beginning of the bounding box (left side) and the width of the bounding box are considered, while the Y axis coordinate and the height of the bounding box predicted by the CNN are ignored.

For enhancing the CNN model robustness and generalization capabilities, a novel data augmentation technique is used, in which each original input image (such as the one in FIG. 17) is split into 10 full width and equally spaced vertical components and then the extracted components are shifted and restacked vertically together).

Figure 19:
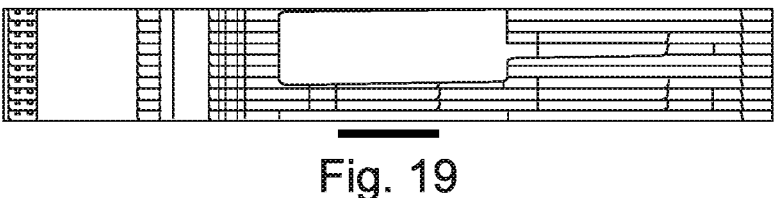
FIG. 19 shows the network output with a line below the image indicating the plasma layer.

FIG. 19 shows the network output with a line below the image indicating the plasma layer. The output is the left and right boundary of the plasma layer corresponding to the upper and lower end of the plasma layer in the container.

The network predicts two coordinates for each cell, tx and tw. While in the original implementation, the network also predicts ty and th, used for computing the bounding box height and center, we do not need these predictions, as the height of the bounding box is fixed and spans the entire height of the image.

Figure 20:
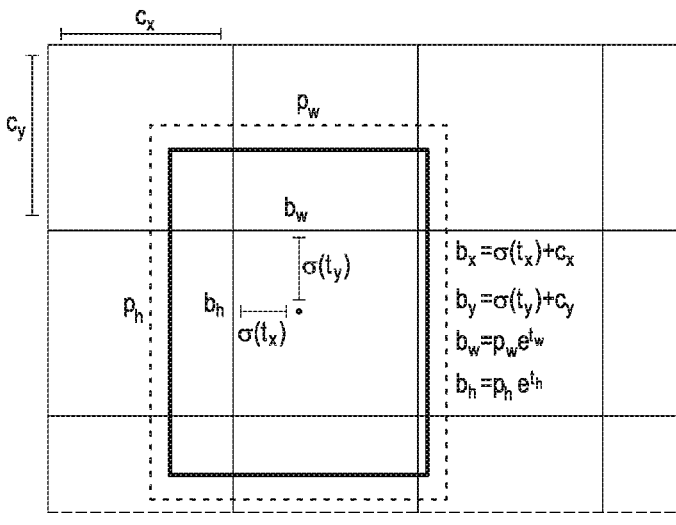
FIG. 20 illustrated a cell offset from the top left corner of the image by (cx, cy) and the bounding box prior has width pw in accordance with an embodiment of the present invention.

If the cell is offset from the top left corner of the image by (cx, cy) and the bounding box prior has width pw, then the predictions correspond to (FIG. 20):

$$bx = \sigma(tx) + cx$$

$$bw = p_w e^{tw}$$

During training, anchors are used for predefining boxes. $p_w$ is the anchor width. For each location of the 3-level FPN, two anchors are distributed as follow: the lower level FPN with anchors (119,160) and (154,160), the mid-level FPN (40,160) and (57,160) and high-level FPN (78,160), (97, 160), where the first coordinate is the anchor width and the second is the anchor height. For learning tx and tw, the sum of squared error loss is used in training.

The network predicts an objectness score for each bounding box using logistic regression. This should be 1 if the bounding box prior overlaps a ground truth object by more than any other bounding box prior. Lastly, the network predicts a class probability. In our case, we currently use only one class, which is plasma. Binary cross entropy loss is used for training the objectness and class probability.

During inference, bx and bw are determined for each location. Then, by objectness is thresholded, if the objectness is lower than a threshold (0.5), we remove the box. Finally, the box with the lower class confidence is removed if two bounding boxes of the same class having intersection over union larger than a threshold are present.

The advantages of a method according to the present disclosure relate in a first aspect to a reduction of human failure as the user does not have to learn and follow special rules to sort container into specific racks that might just differ by their barcodes and not in any physical properties.

In a further aspect, the advantages of a method according to the present disclosure relate to a reduction of rack types and a better usability as the system can determine the container type or class in a generalized way so that no classical discriminators like rack barcodes are required. Only container with significant difference in their outer dimensions will have to be sorted into specific racks that are able to accommodate them.

An important advantage of a method according to the present disclosure is, that the system can measure dimensions and to determine cap and false bottom in a generalized way by CNN. It is not required to retrain the network in order to introduce new container types or classes.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

REFERENCE NUMERALS 2 front illumination system
3 back illumination system
5 camera
7 mirror
10 rack
12 container
14 rack insert
15 background light
d distance between camera and rack
20 image sensor
25 imaging objective lens
30 TIR element
40 LED stripes
42 doped Perspex
44 reflective film
45 diffusing film

What is claimed is:

1. A method for determining characteristics of a sample container in an automated testing system, the method comprising the steps of:
    identifying the presence of a rack within the automated testing system;
    capturing at least one image of the rack using a sensor of the automated testing system;
    processing the at least one image to determine that the rack comprises at least one container;
    processing the at least one image to determine one or more characteristics of the container selected from the group consisting of width, height, shape, and presence of a cap;
    processing the at least one image to determine presence or absence of a false bottom of the container;
    determining a type or class of the container based at least on the one or more characteristics of the container; and
    capturing at least a second image of the rack, measuring height, width, or both of the container at different heights in each image, and calculating mean values with standard deviation for determining the container's dimensions.

2. The method according to claim 1, wherein determining the type or class of the container based on the one or more characteristics of the container comprises identifying the type or class of the container using container data stored in a database, and wherein the database further comprises a set of instrument parameters assigned to a container type or container class.

3. The method according to claim 1, wherein presence of the container is determined by determining intersection points of a top of the rack and a background illumination by identifying a 2D pixel intensity matrix in different sections in the at least one image where the background illumination is present, followed by a first-order differentializing for identifying a slope in the intensity profile.

4. The method according to claim 3, wherein the 2D pixel intensity matrix is convolved to reduce noise in the image.

5. The method of claim 4, wherein the 2D pixel intensity matrix is converted to a 1D matrix by taking an average along each row and an intensity plot and variance of the 1D matrix is used for determining the presence of the container.

6. The method of claim 1, wherein the image is classified into one of two classes by a convolutional neural network (CNN).

7. The method of claim 1, wherein determining the type or class of the container comprises determining presence or absence of a false bottom of the container by comparing the position of the container's inner lower end with the position of a bottom end of the rack or the bottom end of a rack insert.

8. The method of claim 1, further comprising illuminating the container using a light source positioned to illuminate a first side of the rack opposite a second side of the rack, wherein the sensor is arranged to capture an image of the second side of the rack.

9. The method according to claim 8, wherein a width for illumination of the container is in a range between 15 to 35 mm.

10. The method according to claim 8, wherein the light source comprises LEDs arranged in two opposite arranged LED stripes.

11. The method of claim 1, further comprising:
    determining a region of interest (ROI) in the at least one image by identifying reference points;
    determining an upper end of the rack in the ROI; and
    determining edges of an upper end of the container within the ROI.

12. The method of claim 1, wherein determining presence or absence of the false bottom of the container is based on comparing a position of the container's inner lower end with the position of a bottom end of the rack or a bottom end of an insert of the rack.

13. The method of claim 1, wherein determining presence or absence of the false bottom of the container further comprises capturing a plurality of images of the container while rotating the container, and processing the plurality of images to determine presence or absence of the false bottom.

14. A method for determining characteristics of a sample container in an automated testing system, the method comprising the steps of:
    identifying the presence of a rack within the automated testing system;
    capturing at least one image of the rack using a sensor of the automated testing system;
    determining that the rack comprises at least one container;
    determining, based on the at least one image, one or more characteristics of the container selected from the group consisting of width, height, shape, and presence of a cap;
    determining, based on the at least one image, presence or absence of a false bottom of the container;
    determining a type or class of the container based at least on the one or more characteristics of the container;
    determining boundaries of separated layers of a material located in the container;
    determining hematocrit based on one or more of layers, liquid levels, or liquid volumes percentage of a first layer and a second layer in the one container; and
    capturing multiple images of the container during rotation of the container in front of the sensor and forming a segmented picture from the multiple images.

15. The method of claim 14, wherein the first layer comprises red blood cells and the second layer comprises plasma.

16. The method of claim 14, further comprising the step of applying the segmented picture to a convolutional neural network (CNN) for determining an upper boundary and a lower boundary of a plasma layer in the segmented picture for generating a bounding box enclosing the plasma layer in all segments of the segmented picture.

17. The method of claim 16, comprising the step of rearranging the segments of the segmented picture prior to determining again the upper boundary and the lower boundary of the plasma layer in the newly arranged segmented picture for generating a bounding box enclosing the plasma layer in all segments of the segmented picture.

18. A system for determining characteristics of a container in a rack for an automated testing system, the system comprising:

a sensor configured to capture one or more images of a first side of the rack;

a processor configured to receive the one or more images; to process the one or more images to determine one or more characteristics of the container selected from the group consisting of width, height, shape, and presence of a cap; and to process the one or more images to determine presence or absence of a false bottom of the container;

a light source configured to provide back illumination by illuminating a second side of the rack opposite the first side of the rack; and comprising a second light source configured to provide front illumination by illuminating the first side of the rack, and wherein the first light source and the second light source each comprise an LED stripe.

19. The system of claim 18, further comprising a database comprising characteristics of a plurality of containers, and wherein the processor is further configured to determine a type or class of the container based on the one or more characteristics of the container and information of the characteristics of the plurality of containers from the database.

20. The system of claim 18, wherein the sensor is a camera selected from the group consisting of a monochrome CMOS sensor and a color sensor.

\* \* \* \* \*